United States Patent [19]

Johnson

[11] Patent Number: 4,550,869
[45] Date of Patent: Nov. 5, 1985

[54] DOUBLY ELASTIC CUSHIONED CARRYING STRAP

[76] Inventor: Joyce E. Johnson, 631 E. Washington, Pontiac, Ill. 61764

[21] Appl. No.: 578,017

[22] Filed: Feb. 8, 1984

[51] Int. Cl.⁴ .............................................. A61F 5/40
[52] U.S. Cl. .................................... 224/202; 224/264; 224/257; 128/94
[58] Field of Search .................. 128/94; 224/202, 264, 224/257

[56] References Cited

U.S. PATENT DOCUMENTS

| | | | |
|---|---|---|---|
| 883,004 | 3/1908 | Dingman | 128/94 |
| 3,371,663 | 3/1968 | Apgar | 128/94 |
| 3,554,194 | 1/1971 | Johnson | 128/94 |
| 4,324,012 | 4/1982 | Cannaday | 224/264 |

*Primary Examiner*—Stephen Marcus
*Assistant Examiner*—David Voorhees
*Attorney, Agent, or Firm*—McCaleb, Lucas & Brugman

[57] ABSTRACT

A cushioned carrying strap comprises a rectangular cross-section tube of flexible material such as leather, vinyl, or canvas, a plurality of individual pads or blocks of elastic cushioning material such as foam rubber disposed in closely-adjacent substantially abutting relationship in a load-bearing section of the tube, and a stitched or otherwise suitable connection adhering opposite portions of the tube together immediately fore and aft of each elastic pad or block to form individual, adjacent pockets to hold them in discrete, closely adjacent positions lengthwise of the tube and thereby provide a substantially continuous, cushioned portion of the strap which is elastically deformable under load in both transverse and longitudinal directions relative to the length of the tube.

2 Claims, 11 Drawing Figures

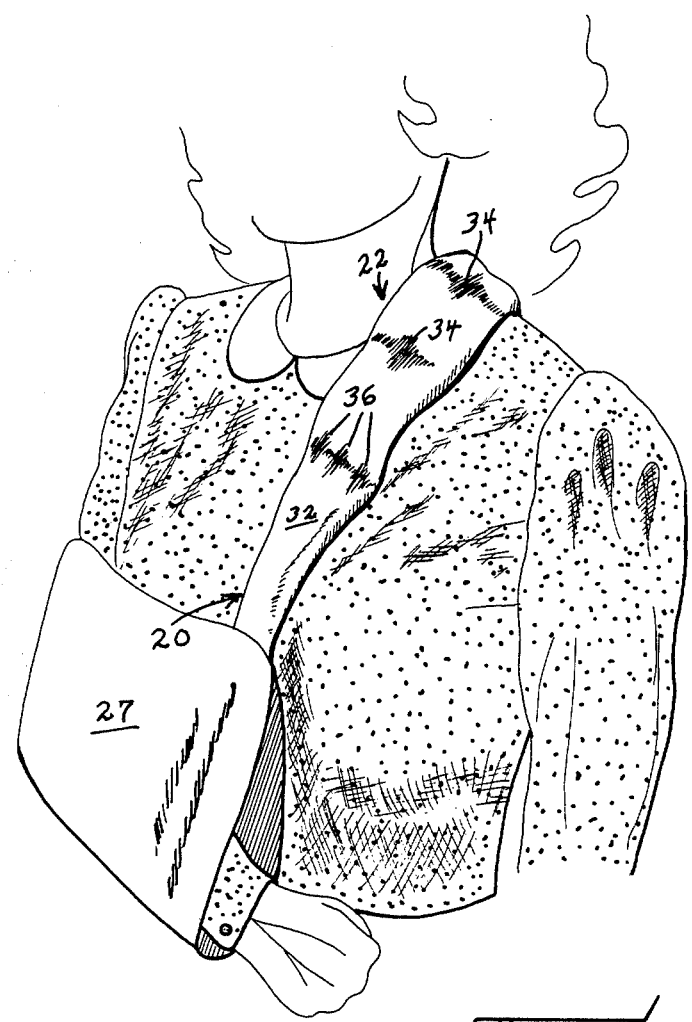

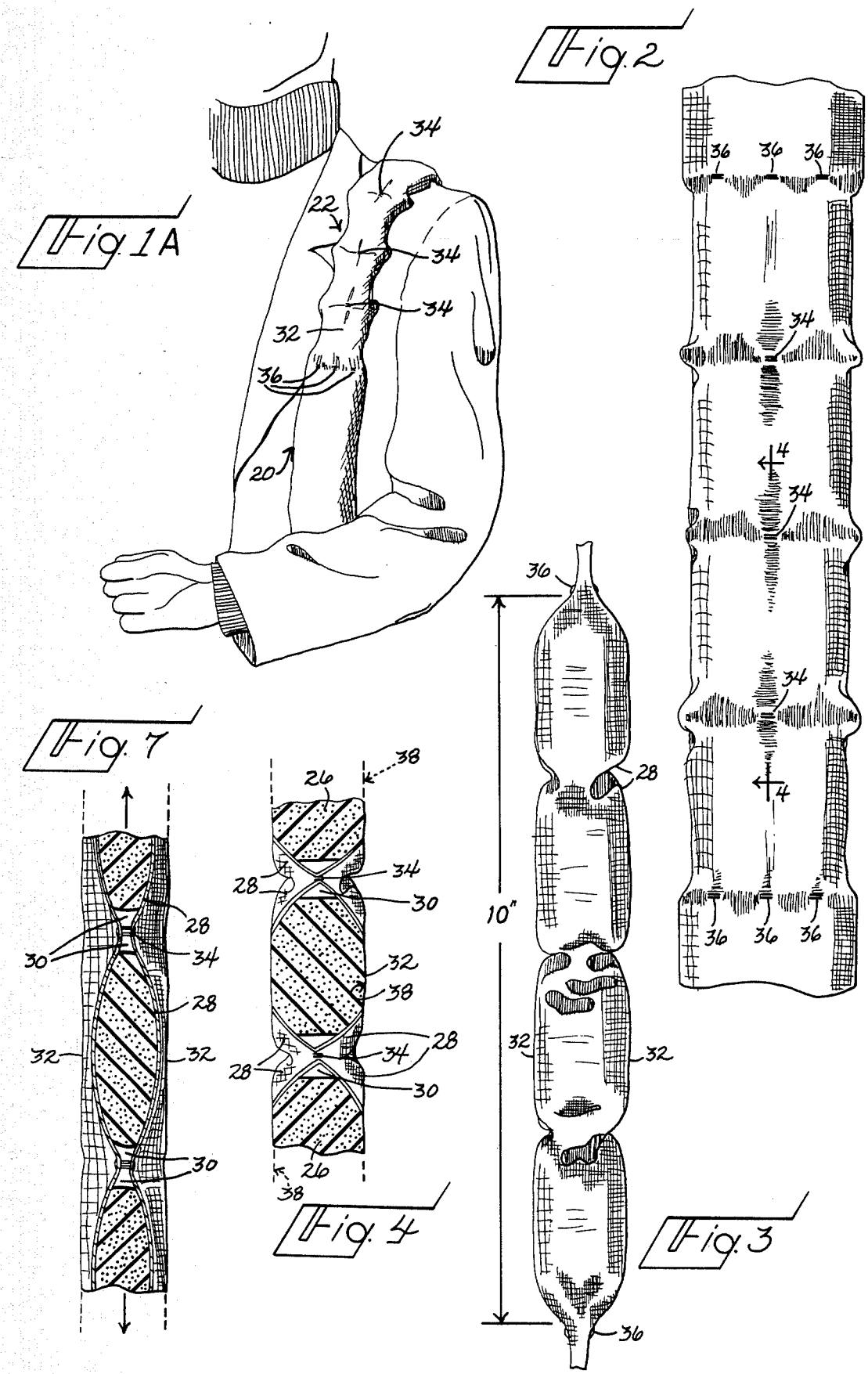

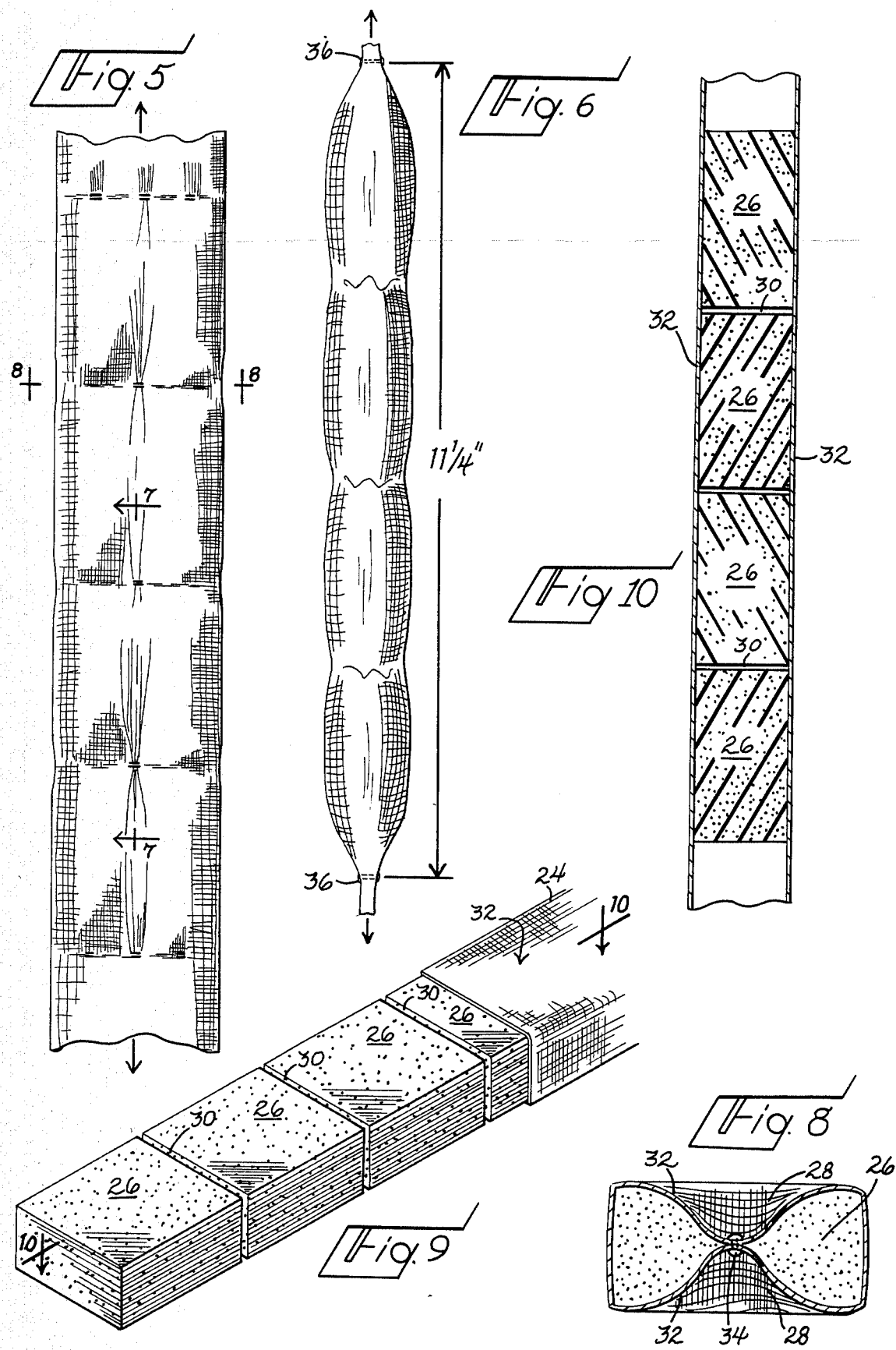

DOUBLY ELASTIC CUSHIONED CARRYING STRAP

BACKGROUND OF THE INVENTION

The invention relates generally to carrying straps and more particularly to cushioned straps especially suitable for use as shoulder and body straps on golf, mail, and luggage bags, back packs and baby carriers, slings for rifles and broken arms, animal collars, restraints and lifting harnesses, and a wide variety of other uses where a load is applied by a strap, surcingle or the like to a human or animal body.

Typcially, rubber or rubber-like foam material is used on or in shoulder straps and the like to spread the load and relieve pressure points on bone and tissue. While such straps are generally acceptacle, they have some disadvantages especially from the standpoint of comfort for long time wear or use. Some have a cushioned shoulder pad located along a strap at a load-bearing position but have a relatively stiff backing which presses into the user'neck, shoulder, collar bone and spine, and becomes uncomfortable with extended use; examples are the shoulder strap pads illustrated in U.S. Pat. Nos. 3,154,787 and 4,401,246; British Pat. No. 527,910; and Swiss Pat. No. 173,225. Some have a strap completely or partially in tubular form filled with cushioning material; examples are shown in U.S. Pat. No. 3,882,914, Swiss Pat. No. 63244 and French Pat. No. 1365328.

While these prior straps have user-contacting, load-bearing portions which are soft and indentible to varying extents in a transverse direction, they all have the drawback that they are inelastic lengthwise. It is my belief that lack of elasticity in this direction is an important factor in causing discomfort after extended use, as for example where a shoulder sling supports a broken arm during all a person's waking hours for several weeks or a rifle sling is supported on a soldier's or a sportsman's shoulder on a long trip. I have observed that, no matter how soft the padding is on such a strap, if the strap itself is inelastic, fatigue and discomfort results from the inability of the strap to "give" as the user's shoulder bobs up and down in a normal walking pace. This affects different people to different extents depending on the shoulder and muscle tissue development over their bones and their general physical condition, but after a while, they find it a great relief to take the loaded strap off their shoulder and allow it to rest.

SUMMARY OF THE INVENTION

I have discovered that, for long term comfort, a shoulder strap, body harness strap, or the like, in addition to having a cushioned surface distributing the load over the muscles and tissues, should have a substantial degree of lengthwise elasticity. By flexing lengthwise, as the user's shoulder bobs up and down, in normal movements, sharp pressure peaks between the cushioned strap surface and the user's body are prevented, and the pressure load on the bones, muscles and tissue can be evened out and maintained at a value sufficiently low to be readily adsorbed by the cushioned portion of the strap, for long term comfort.

Accordingly, a general object of the invention is to provide a carrying strap with a body-contacting portion which has both transverse and longitudinal elasticity.

Another object of the invention is to provide a supporting strap with a cushioned, load-bearing section having a plurality of individual, closely adjacent, substantially abutting elastic pads or blocks in a flexible tube with opposite sides of the tube folded together and connected to one another at opposite ends of the individual pads to hold them at discrete positions in individual, adjacent pockets.

Another object of the invention is to provide accordion-like folds or pleats in the flexible tube and to interconnect these folds or pleats at opposite ends of the individual pads allowing minimal air space at each end of each pad, thus enabling the cushioned, load-bearing portion of the strap to stretch under tension by separating, deflecting, and displacing the pads and tending to straighten the folds.

Another object is to provide the elastic pads in the form of individual blocks of elastic material of rectangular cross-section having a thickness at least half the width thereof to make room for substantial-sized folds or pleats of the flexible tube extending inwardly to connecting points between pads.

BRIEF DESCRIPTION OF DRAWINGS

Other objects and advantages will be apparent from the following description taken in connection with accompanying drawings in which:

FIG. 1 is a fragmentary perspective view of a cushioned carrying strap illustrating a shoulder-supported version of the present invention in the form of a sling for a broken arm;

FIG. 1A is similar to FIG. 1 showing an alternate embodiment of the invention applied to the sling for a rifle, a shoulder strap for a golf, mail or luggage bag or the like.

FIG. 2 is a plan view of the user-contacting, load-bearing portion of the strap in untensioned, non-load-bearing condition with the folds or pleats maximized between adjacent elastic pads or blocks;

FIG. 3 is a side view of FIG. 2;

FIG. 4 is a fragmentary cross-sectional view of FIG. 2, taken along line 4—4;

FIG. 5 is a plan view similar to FIG. 2, showing the user-contacting, load-bearing portion stretched under a tensile load with the folds or pleats substantially straightened out;

FIG. 6 is a side view of FIG. 5;

FIG. 7 is a longitudinal cross-sectional view similar to FIG. 4, taken along line 7—7 of FIG. 5;

FIG. 8 is a transverse cross-sectional view of FIG. 5, taken along line 8—8;

FIG. 9 is an initial assembly view showing an early stage in manufacturing the strap before the folds or pleats are formed between the adjacent cushioned pads or blocks; and FIG. 10 is a longitudinal sectional view of FIG. 9 taken on line 10—10.

DESCRIPTION OF THE PREFERRED EMBODIMENT

Referring now to the two specific embodiments of the invention shown in FIGS. 1 and 1A of the drawing, the cushioned carrying strap generally designated 20 consists of a band having a user-contacting, load-bearing portion 22 which is elastic in both transverse and longitudinal directions according to the present invention.

The strap comprises a tube 24 of flexible, fabric-like material and a plurality of individual pads or blocks 26 of elastic cushioning material.

While the tube 24 of fabric-like material is flexible, it should preferably be relatively non-elastic to carry tensile loads. For example, leather or fabric-backed vinyl plastic may be used on shoulder slings for rifles and shoulder straps for golf, mail, and luggage bags; and canvas-like fabrics such as washable denim may be used for back-pack harness straps and shoulder straps on slings for broken arms.

The pads or blocks 26 are made of foam rubber or rubber-like material and are preferably substantially thick to make room for accordion-like folds or pleats 28 interconnected between adjacent pads 26; this provides longitudinal elasticity in the user-contacting, load-bearing portion 22 even though the fabric material 24 is itself not stretchable, as will be described. Pads 26 with a thickness of 50% or more of their width are preferred for many applications. As one example, 2" wide by 1" thick foam rubber pads have been used with excellent results in denim tubes, as described above, to provide slings for broken arms. One such cushioned supporting strap with a sling 27 is illustrated in FIG. 1; another, general purpose, sling version of this invention is shown in FIG. 1A for rifles, bags and the like. As stated above, the tube 24 is made of denim and contains in the example shown a plurality of individual pads or blocks of foam rubber which may for example be 2" square and 1" thick in the cushioned portion 22. The tube is preferably sized so the elastic pads 26 fit snugly within it, but without significant initial compression.

As best shown in FIGS. 9 and 10, the first step in making the cushioned strap 20 is to fit the elastic pads 26 within the denim tube 24 in nearly abutting relationship, but with a small air space 30 between adjacent pads, enabling the opposite long walls 32 of the tube to be sewn or otherwise adhered together. As best shown in FIGS. 4, 7, and 8, the opposite long walls 32,32 of the denim tube are sewn together by a stitch 34 between each of the adjacent pads 26. The end pads 26 are held by triple stitches 36. The air spaces 30 between the pads are very important in forming the folds or pleats 28 which provide substantial longitudinal elasticity for the cushioned strap.

Thus the stitches 34 and 36 comprise combined fold-producing and connecting means drawing opposite sides 32,32 of the denim tube together and provide individual, closely adjacent pockets 38 to hold the elastic pads in discrete, closely adjacent, end-to-end positions lengthwise of the tube. This provides a substantially continuous surface for the load-bearing portion 22 and make it elastically deformable in both transverse and longitudinal directions relative to the length of the tube. Alternatively, other means such as suitable fabric adhesive, or staples, may be substituted for the stitched connections.

FIGS. 3 and 4 show an actual prototype of the cushioned load-bearing portion 22 of the above-described strap, in an untensioned condition. This measured ten inches between the stitches 36,36, as shown in FIG. 3. When tensioned, as shown in FIGS. 6 and 7, the ten inch section stretches to eleven and one-fourth inches as shown in FIG. 6. In other words, although the denim fabric itself, for all practical purposes, is non-stretchable, it becomes elastic in the longitudinal direction as a result of the present construction employing the accordion-like folds or pleats 28 and air pockets 30 in combination with the slightly-compressed elastic pads 26 filling the individual pockets 38.

In use, as shown in FIG. 1, the cushioned strap portion 22 is transversely indentible to spread the load over the bones, muscles and tissues in the user's shoulder, neck, collar bone and spine. In addition, as the user's shoulder bobs up and down at a normal walking or hiking pace, the portion 22 repeatedly stretches and contracts to eliminate or moderate peak loads applied to the user's shoulder and stress points and thereby maintains the tension at a substantially uniform value without cyclic pressure peaks coinciding with the user's walking pace. This allows the cushioned portion 22 to stretch, reduce fatigue, and enable the user to carry a load on a shoulder strap for an extended period of time.

The embodiment described and shown to illustrate the present invention has been necessarily specific for purposes of illustration. Alterations, extensions, and modifications would be apparent to those skilled in the art.

The embodiments of the invention in which an exclusive property or privilege is claimed are defined as follows:

1. A cushioned carrying strap having a user-contacting, load bearing portion intermediate the ends thereof which is cushioned and elastic primarily in a longitudinal direction, said load-bearing portion comprising:

a plurality of individual elastic blocks of elastic cushioning material linearly disposed in a closely-adjacent, nearly abutting relationship;

a tube of non-stretchable, flexible material snugly enclosing said blocks;

said tube being disposed intermediate the ends of the hand and subject to tension applied at opposite ends of the band and to transverse loads when tensioned about a user's shoulder;

said tube having laterally extending accordion-like pleats between adjacent blocks, the tube normally having a bulge extending laterally outward of the tube in opposite directions at each location of a pleat, the bulges each containing a continuation of the pleat; and connecting means drawing opposite sides of said tube together at each end of each elastic block to maintain the accordion-like pleats between adjacent blocks and hold the blocks in discrete, closely adjacent positions lengthwise of the tube thereby enabling two-way elasticity resulting from substantial elastic stretch of the tube by unfolding said pleats concurrently with elastic deformation transverse to the tube in response to tension applied to the ends of the tube.

2. A cushioned carrying strap according to claim 1 in which the corners of the elastic blocks are substantially square and the cross-section of the tube is substantially rectangular with square corners to thereby substantially fill said tube with elastic cushioning material.

* * * * *